US012741006B2

(12) United States Patent
Sardeshmukh et al.

(10) Patent No.: US 12,741,006 B2
(45) Date of Patent: Sep. 22, 2026

(54) HERBO-LIPID COMPOSITION AND THE PROCESS FOR PREPARATION THEREOF

(71) Applicant: Sadanand Prabhakar Sardeshmukh, Pune (IN)

(72) Inventors: Sadanand Prabhakar Sardeshmukh, Pune (IN); Vineeta Vasant Deshmukh, Pune (IN)

(73) Assignee: Sadanand Sardeshmukh, Pune (IN)

( * ) Notice: Subject to any disclaimer, the term of this patent is extended or adjusted under 35 U.S.C. 154(b) by 1096 days.

(21) Appl. No.: 17/609,643

(22) PCT Filed: Feb. 12, 2020

(86) PCT No.: PCT/IB2020/051119
§ 371 (c)(1),
(2) Date: Nov. 8, 2021

(87) PCT Pub. No.: WO2020/225611
PCT Pub. Date: Nov. 12, 2020

(65) Prior Publication Data

US 2022/0211794 A1 Jul. 7, 2022

(30) Foreign Application Priority Data

May 7, 2019 (IN) ............................ 201921018274

(51) Int. Cl.

| | |
|---|---|
| ***A61K 36/00*** | (2006.01) |
| ***A61K 35/20*** | (2006.01) |
| ***A61K 36/24*** | (2006.01) |
| ***A61K 36/736*** | (2006.01) |
| ***A61K 36/899*** | (2006.01) |

(52) U.S. Cl.
CPC ............ *A61K 36/899* (2013.01); *A61K 35/20* (2013.01); *A61K 36/24* (2013.01); *A61K 36/736* (2013.01); *A61K 2236/15* (2013.01); *A61K 2236/31* (2013.01); *A61K 2236/53* (2013.01)

(58) Field of Classification Search
CPC ...... A61K 36/899; A61K 35/20; A61K 36/24; A61K 36/736
See application file for complete search history.

(56) References Cited

U.S. PATENT DOCUMENTS 12,201,660 B2 * 1/2025 Sardeshmukh ........... A61P 1/08

FOREIGN PATENT DOCUMENTS

| | | | |
|---|---|---|---|
| IN | 20080080811 | * | 8/2016 |
| KR | 20140040359 A | * | 4/2014 |
| WO | WO2017218853 A1 | * | 12/2017 |
| WO | WO2018142429 A1 | * | 8/2018 |

OTHER PUBLICATIONS

Deshpande, A., "Assessment of Effect of CG4 (An Ayurvedic Formulation) in the Management of Side Effects of Chemotherapy in Breast Cancer", A thesis submitted to Tilak Maharashtra Vidyapeeth, Pune For the Degree of Doctor of Philosophy (Ph.D) Month & Year: Dec. 2016, 196 pp.(esp. p. 76, Table. 7) (Year: 2016).*
Deshpande, A., "Assessment of Effect of CG4 (An Ayurvedic Formulation) in The management of Side Effects of Chemotherapy in Breast Cancer", A thesis submitted to Tklak Maharahtra Vidyapeeth, Pune For Degree of Doctor of Philosophy (Ph.D) Month & Year: Dec. 2016, 196 pp (especially p. 69, Table 7) (Year: 2016).*
Machine translation of KR20140040359A (Year: 2014).*
Machine translation of WO2018142429A1 (Year: 2018).*
Machine translation of IN20080080811 (Year: 2016).*
Machine translation of WO2017218853A1 (Year: 2017).*
Deshpande, A., "Assessment of Effect of CG4 (An Ayurvedic Formulation) in The Management of Side Effects of Chemotherapy in Breast Cancer", A thesis submitted to Tilak Maharashtra Vidyapeeth, Pune For the Degree of Doctor of Philosophy (Ph. D. ) Month & Year: Dec. 2016.
TKDL database: Abstract Id: RS24/252, Title: Gaja Bahyakrmihara Durvadi Lepa, Bibliography: Gajyurveda Knowledge Known Since: 1000 years.
PCT International Search Report for International Application No. PCT/IB2020/051119, completed Jul. 31, 2020, 2pp.
PCT Written Opinion for International Application No. PCT/IB2020/051119, completed Jul. 31, 2020, 4pp.

* cited by examiner

*Primary Examiner* — Russell G Fiebig
(74) *Attorney, Agent, or Firm* — The Roy Gross Law Firm, LLC; Roy D. Gross

(57) ABSTRACT

The present disclosure relates to a herbo-lipid composition for alleviating symptoms related to inflammation resulting into improved quality of life. The herbo-lipid composition comprises an extract of petals and stalks of Padmak, an extract of whole Durva plant, and decoction of roots of Ananta, which are processed in cow's ghee. The herbo-lipid composition of the present disclosure can be used internally for alleviating symptoms of inflammation mainly in erythematous skin rash. Its topical application is also beneficial in radiotherapy induced adverse effects like burning micturition, burning in vagina, dysuria, diarrhea and pain in lower abdomen in cervical cancer patient and stomatitis, and local burning in oral cancer patients. The composition also helps in reducing radiotherapy and chemotherapy induced adverse effects in various types of cancers when given orally.

8 Claims, 7 Drawing Sheets

HERBO-LIPID COMPOSITION AND THE PROCESS FOR PREPARATION THEREOF

CROSS REFERENCE TO RELATED APPLICATIONS

This application is a National Phase of PCT Patent Application No. PCT/IB2020/051119, having International filing date of Feb. 12, 2020, which claims the benefit of priority of Indian Patent Application number 201921018274, filed May 7, 2019, the contents of which are all incorporated herein by reference in their entirety.

FIELD

The present disclosure relates to a herbo-lipid composition and a process for preparation thereof. Particularly, the present disclosure relates to a herbo-lipid composition for reducing inflammation and its manifestations in various diseases including cancer.

Definitions

As used in the present disclosure, the following terms are generally intended to have the meaning as set forth below, except to the extent that the context in which they are used indicate otherwise.

Padmak: The term "Padmak" refers to "Lotus (*Nelumbo nucifera*)".

Durva: The term Durva refers to "Burmuda grass (*Cynodon dactylon*)".

Ananta: The term Ananta refers to "Swallow root (*Decalepis hamiltonii*) or *Hemidesmus indicus* or *Cryptolepis buchnani* or *Ichnocarpus frutescens.*"

Ghrut: The term "Ghrut" refers to "clarified butter" or "Ghee" prepared from Cow's milk.

Trituration: The term "trituration" refers to either reducing the particle size of a substance or production of a homogeneous material by mixing component materials thoroughly or wet grinding any material with a liquid media like fresh juice or decoction etc.

Karnofsky score: The term "Karnofsky score" refers to the Karnofsky Performance Scale Index allows patients to be classified as to theft functional impairment QoL: Quality of Life QLQ C 30: Quality of Life Questionnaire Symptom score: Symptom score of QLQ is indicative of symptomatology; hence decrease in symptom score represents both decrease in disease related symptoms and adverse effects of conventional treatment.

Function score: Functional score of QLQ signifies status of routine physical activities. Increase in functional scores represents improvement in QoL.

Global score: Global score of QLQ represents overall well-being of a patient. Increase in global scores represents improvement in QoL.BACKGROUND The background information herein below relates to the present disclosure but is not necessarily prior art.

Among the various causes of deaths, cancer ranks next to cardiovascular diseases worldwide. It is expected that deaths due to cancer will increase rapidly over the next two decades. The existing modalities of treatment of cancer include surgery, radiotherapy and chemotherapy.

Chemotherapy is used to reduce the primary tumour load as well as distant metastasis. However, chemotherapy induces adverse side effects such as nausea, vomiting, loss of appetite, diarrhea, constipation, weakness, alopecia (loss of hair) and neurological problems. The side effects are mainly caused by the inability of chemotherapeutic drugs to distinguish between dividing cancer cells and dividing normal cells. These adverse effects interfere with continuation of therapy and result into poor quality of life of patients.

Therefore, there is felt a need to provide a composition that mitigates the aforestated drawbacks.

Objects

Some of the objects of the present disclosure, which at least one embodiment herein satisfies, are as follows:

An object of the present disclosure is to ameliorate one or more problems of the prior art or to at least provide a useful alternative.

Another object of the present disclosure is to provide a herbo-lipid composition.

Yet another object of the present disclosure is to a process for preparing a herbo-lipid composition.

Still another object of the present disclosure is to provide a herbo-lipid composition for alleviating effects of inflammation and its manifestations in various diseases including cancer.

Other objects and advantages of the present disclosure will be more apparent from the following description, which is not intended to limit the scope of the present disclosure.

SUMMARY

The present disclosure provides a herbo-lipid composition comprising an extract of petals and stalks of Padmak, an extract of whole Durva plant, a decoction of roots of Ananta, and Ghee obtained from cow's milk in an amount ranging from 90 wt % to 98 wt % of the total weight of the composition.

The amount of the combined extracts of petals and stalks of Padmak, whole Durva plant, and roots of Ananta is in the range of 2 wt % to 10 wt % of the total weight of the composition.

The weight ratio of the extract of petals and stalks of Padmak to the extract of whole Durva plant to the decoction of Ananta is 1:1:1.

The extract of petals and stalks of Padmak, the extract of whole Durva plant, and the decoction of roots of Ananta are independently obtained by using at least one solvent selected from the group consisting of alcohol, water, and a mixture thereof.

The decoction of Ananta is extract of *Decalepis hamiltonii.*

The present disclosure further provides a process for preparing a herbo-lipid composition. The process comprises blending an extract of petals and stalks of Padmak, an extract of whole Durva plant, and decoction of roots of Ananta, in a predetermined amount of Ghee to obtain a mixture. The mixture is heated at a temperature in the range of 60° C. to 120° C. for a predetermined time to obtain the herbo-lipid composition in the form of thick viscous liquid. The ratio of the petals of flowers of Padmak to the stalk of flowers of Padmak is 3:1, and the ratio of the petals and the stalks of flowers of Padmak to solvent is 1:1.25. The ratio of whole Durva plant to solvent is 1:2. The ratio of roots of Ananta to solvent is 1:8 which is reduced to $\frac{1}{4}^{th}$ during decoction.

BRIEF DESCRIPTION OF THE ACCOMPANYING DRAWING

The present disclosure will now be described with the help of the accompanying drawing, in which.

DETAILED DESCRIPTION

Figure 1:
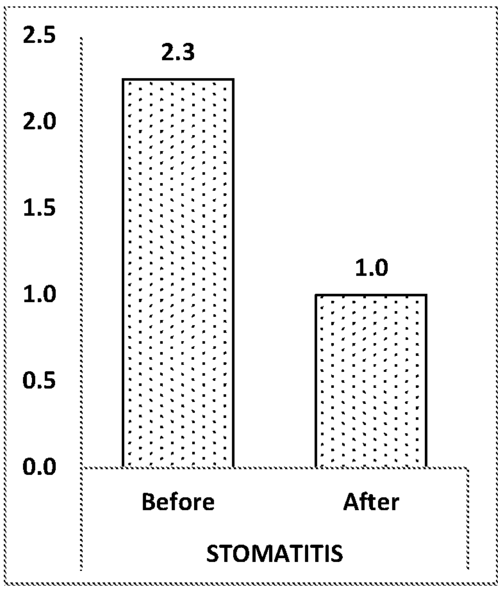
FIG. 1 depicts a graphical representation of the effect of the herbo-lipid composition on stomatitis in oral cancer patients undergoing radiotherapy.

Embodiments, of the present disclosure, will now be described with reference to the accompanying drawing.

Embodiments are provided so as to thoroughly and fully convey the scope of the present disclosure to the person skilled in the art. Numerous details are set forth, relating to specific components, and methods, to provide a complete understanding of embodiments of the present disclosure. It will be apparent to the person skilled in the art that the details provided in the embodiments should not be construed to limit the scope of the present disclosure. In some embodiments, well-known processes, well-known apparatus structures, and well-known techniques are not described in detail.

The terminology used, in the present disclosure, is only for the purpose of explaining a particular embodiment and such terminology shall not be considered to limit the scope of the present disclosure. As used in the present disclosure, the forms “a,” “an,” and “the” may be intended to include the plural forms as well, unless the context clearly suggests otherwise. The terms “comprises,” “comprising,” “including,” and “having,” are open ended transitional phrases and therefore specify the presence of stated features, integers, steps, operations, elements, modules, units and/or components, but do not forbid the presence or addition of one or more other features, integers, steps, operations, elements, components, and/or groups thereof. The particular order of steps disclosed in the method and process of the present disclosure is not to be construed as necessarily requiring their performance as described or illustrated. It is also to be understood that additional or alternative steps may be employed.

The incidence of cancer is increasing worldwide. Chemotherapy is used to reduce the primary tumour load as well as recurrence and metastasis. Although, chemotherapy is an unavoidable line of treatment for cancer, the adverse effects of chemotherapy frequently interfere with the continuation of chemotherapy. The adverse effects are due to generation of oxidative stress, inability to control inflammation, reduction in immune response and functional impairment in tissues. These destructive effects result in impairment of the quality of life of patients.

Therefore, the present disclosure provides a composition that mitigates the aforestated drawbacks.

In an aspect of the present disclosure there is provided a herbo-lipid composition. The composition comprises an extract of petals and stalks of Padmak, an extract of whole Durva plant, decoction of roots of Ananta, and Ghee obtained from cow’s milk in an amount ranging from 90 wt % to 98 wt % of the total weight of the composition.

The amount of the combined extracts of the petals and stalks of Padmak, the extract of the whole Durva plant, and the decoction of roots of Ananta is in the range of 2 wt % to 10 wt % of the total weight of the composition.

The weight ratio of the extract of Padmak to the extract of Durva to the decoction of Ananta is 1:1:1.

The rationale for selecting the individual components of the composition is as follows:

Padmak flowers produce cooling effect, immunomodulatory effect, detoxifying effect and an anti-inflammatory effect. Due to its cooling effect, it eliminates excessive heat in blood and pacifies acidity. The chemotherapy induced adverse effects like burning sensation all over body, fever, and skin discolouration are well managed with medicated cow’s ghee prepared with fresh juice of Padmak flower.

Durva (*Cynodon dactylon*) mainly imparts its cooling effect on the gastrointestinal system (GI system). Thus, it is beneficial to control chemotherapy induced loss of taste and vomiting by pacifying acidity.

Ananta is roots of *Decalepis hamiltonii* (Swallow roots) or *Hemidesmus indicus* or *Cryptolepis buchnani* or *Ichnocarpus frutescens*. In an embodiment, Ananta is *Decalepis hamiltonii* (Swallow roots). *Decalepis hamiltonii* (Swallow roots) is used due to commercial availability, however, it is asserted that *Hemidesmus indicus* or *Cryptolepis buchnani* or *Ichnocarpus frutescens* will equally be effective, alone or in combination with each other. It also imparts similar properties as that of Durva. It additionally improves appetite, detoxifies blood, and controls fever.

Cow’s ghee used for preparing clarified medicated butter itself, has independent medicinal properties. It improves appetite, increases strength, eliminates toxins and excessive heat, and heals ulcers. All these properties of ghee reduce adverse effects due to chemotherapeutic drugs.

Overall, the combined effect of components of the herbo-lipid composition of the present disclosure imparts anti-inflammatory and immunomodulatory action in various diseases as well as reduces internal and external burning sensation. All these four constituents of the herbo-lipid composition of the present disclosure synergistically shows cooling, anti-pyretic, anti-emetic, anti-inflammatory properties and improvement in complexion. Additionally, the composition smoothens gastrointestinal (GI) tract and improves gross as well as micro level absorption, thus improving metabolism. In cancers especially in carcinoma of the cervix, and oral cavity cancers the radiotherapy induced local toxicities I such as local inflammation, secretions, foul smelling, local burning and the like are also being well managed by herbo-lipid composition of the present disclosure. Thus, in cancer patients, the herbo-lipid composition of the present disclosure alleviates the local adverse effects of radiotherapy, and improves the quality of life.

The extract of Padmak, an extract of Durva, and decoction of Ananta are independently obtained by using at least one solvent selected from the group consisting of alcohol, water, and a mixture thereof.

Padmak is *Nelumbo nucifera* belonging to the family Nymphaceae. *Nelumbo nucifera* is found in India, Sri Lanka, virtually all of Southeast Asia, New Guinea and northern and eastern Australia. *Nelumbo nucifera* is obtained from Bharatiya Sanskriti Darshan Trust (BSDT), Wagholi, Pune.

Durva is the common name for *Cynodon dactylon* belonging to the family Poaceae. *Cynodon dactylon* is originated in the Middle East. It is also found in India, Bermuda and North America. *Cynodon dactylon* is obtained from Bharatiya Sanskriti Darshan Trust (BSDT), Wagholi, Pune.

Ananta is roots of *Decalepis hamiltonii. Decalepis hamiltonii* is commonly known as Swallow root. *Decalepis hamiltonii* belongs to the family Apocynaceae. It is found in South India. *Decalepis hamiltonii* is obtained from Bharatiya Sanskriti Darshan Trust (BSDT), Wagholi, Pune.

Cow's Ghee is obtained from Bharatiya Sanskriti Darshan Trust (BSDT), Wagholi, Pune.

The herbo-lipid composition is administered at a dose in a range of 5 gm to 20 gm per day by oral administration or applied externally.

In an embodiment of the present disclosure, the herbo-lipid composition is prepared in the form of a thick viscous liquid.

In another aspect of the present disclosure, there is provided a process for preparing a herbo-lipid composition. The process comprises blending an extract (fresh juice) of the petals and stalks of Padmak, an extract (fresh juice) of whole Durva plant, and decoction of roots of Ananta, in a predetermined amount of cows' ghee to obtain a mixture. The mixture is heated for a predetermined time at a temperature in the range of 60° C. to 120° C. to remove the solvents present in the extracts to obtain the herbo-lipid composition in the form of thick viscous liquid.

In an exemplary embodiment, the mixture is heated to 100° C.

The predetermined time can be in the range of 30 minutes to 120 minutes. In an exemplary embodiment, the predetermined time is 60 minutes.

In an embodiment, the mixture is heated to remove water present in the mixture.

The extract of petals and stalks of Padmak is prepared by obtaining petals and stalks of flowers of Padmak. The petals and stalks of flowers of Padmak are chopped and then grinded in an aqueous or hydroalcoholic solvent to obtain a paste of petals and stalks of flowers of Padmak. The blend is filtered to obtain a filtrate containing the extract of petals and stalks of Padmak. The ratio of the petals of flowers of Padmak to the stalk of flowers of Padmak is 3:1, and the ratio of the petal and stalk of flowers of Padmak to the solvent is 1:1.25.

The extract of Durva is prepared by obtaining whole plant of Durva. The whole plant of Durva is chopped and then grinded in an aqueous or hydroalcoholic solvent to obtain a paste of Durva plant. The blend is filtered to obtain a filtrate containing the extract of whole Durva plant. The ratio of the whole Durva plant to the solvent is 1:2.

The decoction of Ananta is prepared by obtaining dried roots of Ananta. The roots of Ananta are pulverized to coarse powder and then soaked in an aqueous or hydroalcoholic solvent. It is then heated and filtered to obtain a decoction. The ratio of Ananta to the solvent is 1:8 which is reduced to $\frac{1}{4}^{th}$ of the original volume. The decoction is carried out at a temperature in the range of 80° C. to 120° C. In an exemplary embodiment, the solvent is water and the decoction is carried out at 100° C.

The expiry of Padmakadi Ghrut is 2 years.

The foregoing description of the embodiments has been provided for purposes of illustration and not intended to limit the scope of the present disclosure. Individual components of a particular embodiment are generally not limited to that particular embodiment, but, are interchangeable. Such variations are not to be regarded as a departure from the present disclosure, and all such modifications are considered to be within the scope of the present disclosure.

The present disclosure is further described in light of the following experiments which are set forth for illustration purpose only and not to be construed for limiting the scope of the disclosure. The following experiments can be scaled up to industrial/commercial scale and the results obtained can be extrapolated to industrial scale.

EXPERIMENTAL DETAIL

Example 1: Process for Preparing the Herbo-Lipid Composition (Padmakadi Ghrut) in Accordance with the Present Disclosure The herbo-lipid composition (PDG) was prepared in accordance with the following steps:

Step I: Preparation of Extract of Petals and Stalks of Flower of Padmak (*Nelumbo nucifera*)

330 gm of petals and stalks of flowers of Padmak (*Nelumbo nucifera*) were obtained. The petals and stalks of flower of *Nelumbo nucifera* were chopped in pieces wherein the petal to stalk ratio was 3:1 and mixed with water to have the petals and stalks of *Nelumbo nucifera* to water ratio as 1:1.25. The chopped pieces of petal and stalks of flowers of *Nelumbo nucifera* and water were grinded in a mixer grinder and filtered through a muslin cloth to obtain an aqueous extract of petals and stalks of flowers of *Nelumbo nucifera*, which was used in the preparation of the herbo-lipid composition.

Specifications of Fresh Juice of Padmak:

Description: Dirty white opaque watery liquid pH: 5-6

Weight per ml: 1.004-1.007 gm/ml

Step II: Preparation of Extract of Whole Durva Plant (*Cynodon dactylon*)

Separately, 330 gm of whole plant of *Cynodon dactylon* was obtained and chopped into pieces. The chopped Durva plants were grinded by adding 660 ml water to obtain a blend, wherein the ratio of *Cynodon dactylon* to water was 1:2. The blend was filtered to obtain a filtrate containing extract of Durva which was used in the preparation of the herbo-lipid composition.

Specifications of fresh juice of Durva:

Description: Dirty green colour opaque watery liquid
pH: 4.5-6
Weight per ml: 1.009-1.010 gm/ml Step III: Preparation of decoction of roots of Ananta (*Decalepis hamiltonii*)

Further, 330 gm of roots of Ananta (*Decalepis hamiltonii*) were obtained and grinded to obtain coarse powder (within range of 250-350 microns). It was subjected to decoction, wherein the ratio of *Decalepis hamiltonii* root to water was 1:8 and reduced to ¼$^{th}$ to obtain decoction of *Decalepis hamiltonii*, which was used in the preparation of herbo-lipid composition.

Specifications of decoction of Ananta:

Description: Dirty white opaque watery liquid
pH: 4-5
Weight per ml: 1.010-1.030 gm/ml Preparation of PDG:

The aqueous extract (fresh juice) of flower petals and stalks of *Nelumbo nucifera* (obtained in the step I), aqueous extract (fresh juice) of whole plant of *Cynodon dactylon* (obtained in step II), decoction of roots of *Decalepis hamiltonii* (obtained in step Ill), and clarified butter prepared from cow's milk were mixed in a proportion as given in Table 1. The mixture was heated uniformly at 100° C. for 60 minutes to evaporate water completely to obtain 1 kg of the herbo-lipid composition of the present disclosure. Complete evaporation of water was tested by wick test.

The components of the herbo-lipid composition are given in Table-1.

TABLE 1

Components of the herbo-lipid composition Padmakadi Ghrut (PDG)

| Sr. No. | Contents | Common Name | Quantity for 1 kg batch of finished product-Batch 1 | Quantity for 1 kg batch of finished product-Batch 2 | Quantity for 1 kg batch of finished product-Batch 3 |
|---|---|---|---|---|---|
| 1 | An aqueous extract of *Nelumbo nucifera* | Padmak | 333.33 ml | 250 ml | 400 ml |
| 2 | An aqueous extract of *Cynodon dactylon* | Durva | 333.33 ml | 250 ml | 400 ml |
| 3 | Decoction of *Decalepis hamiltonii* | Ananta | 333.34 ml | 250 ml | 400 ml |
| 4 | Clarified butter | Ghrut, Ghrita, Cow ghee | 950 g | 970 g | 900 g |

Specification of the Herbo-Lipid Composition of the Present Disclosure

Description: Greenish semi-solid granular (mass) paste
Specific gravity at 25° C.: 0.9040 to 0.9140
Refractive index at 25° C.: 1.535 to 1.545
Acid value: 1.3500 to 1.7500
Saponification value: 300 to 370
Unsaponifiable matter: 0.5 to 4
Iodine value: 25 to 45
Peroxide value: 0.5 to 1.5
Congealing point: 27 to 31
RM (Reichert-Meissel) value: 5 to 50
Moisture content: 0 to 0.5%

The below mentioned studies have been conducted for the herbo-lipid composition of batch of finished product 1.

Example 2

Case Study

A 56 years old female patient had sudden onset of erythematous skin rash on Right Median aspect of right forearm on Mar. 11, 2017. She had grade II local pain (Ref. for grading—CTCAE Version 4.0). She was also suffering from the associated symptoms like grade II malaise (Ref. for grading—CTCAE Version 4.0), grade II insomnia (Ref. for grading—Insomnia Severity Index—www.myhealth.va.gov) and grade II burning sensation in whole body (Ref. for grading—CTCAE Version 4.0). The patient was treated by the inventor on the fourth day of symptom development.

She was clinically examined and investigated for Hemogram. As per CTCAE version 4.0, grading of rash was 2, as it was associated with psychological impact causing insomnia and was limiting instrumental activities of daily living such as restricted and painful movements of arm and related activities. The rash being small, rose over the area of skin (less than 5 mm), having domed top and distinct border, was termed as papular rash. Hemoglobin (12.4 gm %), WBC count (4400/ml) and Platelet count (231000/ml) were within normal limits.

A detailed case history of the patient was taken from Ayurvedic perspective especially considering her Prakruti, diet, lifestyle, past illness and previous medication. She had Pitta dominant Kapha constitution, which is prone to inflammations at various body parts as well as tendency towards hyperacidity. She had previous history of Jaundice 30 years back and Herpes zoster on chest region 3 years back. She was also suffering from hyperacidity. 2 months before the incidence of rash, she was under the coverage of various broad spectrum antibiotics for ulcerative wounds on leg due to road accident.

According to Ayurvedic diagnosis, vitiation of Pitta Dosha and Rakta Dhatu were responsible for the development of Pitta dominant skin rash in her case.

The herbo-lipid composition of the present disclosure was selected as a treatment of choice considering its Pitta pacifying, cooling, and anti-inflammatory action. The herbo-lipid composition of the present disclosure was administered orally in a dose of 5 gm each, thrice a day for a period of 2 months.

Results:

The Patient had complete relief in insomnia (from grade II to grade 0) on the first day of administration of the herbo-lipid composition of the present disclosure, whereas her malaise was completely relieved (from grade II to grade 0) 4$^{th}$ day onward upon treatment. Erythema of papular rash was resolved on 4th day (from grade II to grade 0). The rash completely disappeared within a week and local pain (from grade II to grade 0) was completely relieved within 10 days of the treatment with the herbo-lipid composition of the present disclosure. She experienced complete relief in burning sensation in whole body (from grade II to grade 0). The Patient was further happy to report that her general inertia towards urination and peristaltic movements of bowel was normalized, made smooth and satisfactory. In her opinion, her energy level and feeling of well-being were remarkably improved during the course of treatment.

Example 3

Experiment 1—Efficacy Studies of Local Application of the Herbo-Lipid Composition of the Present Disclosure on Radiotherapy Induced Local Adverse Effects in Oral Cancer Patients The herbo-lipid composition of the present disclosure helps in alleviating local adverse effects of radiotherapy by local application in oral cancer patients. To study this, the grades of adverse effects induced by radiotherapy were recorded before and after local application of the herbo-lipid composition of the present disclosure as per Common Terminology Criteria for Adverse Events (CTCAE) version 4.03, as and when the effects appeared in the patients during and after radiotherapy. The treatment of the herbo-lipid composition of the present disclosure was given for a period of 5-7 weeks based on the duration of radiotherapy.

In this study, 8 oral cancer patients undergoing radiotherapy treatment were enrolled.

Assessment:

1. Assessment of adverse effects clinically and grading using CTCAE 4.03 Version (Grading of symptoms on 0 to 4 scales). Lower scale denotes less severity of the symptoms.
2. Assessment of Quality of Life (QoL) using selected questions (31-42, 44, 49) applicable for assessment of local symptoms from Questionnaire—Quality of Life Questionnaire Head and Neck (QLQ H&N) 35 of European Organization for Research and Treatment of Cancer (EORTC) determined on the basis of patients' own perspective about his/her own well-being.

The assessment was performed before the start of the treatment and at the end of the treatment. The data was analyzed as mean values of grades of individual symptoms and increase/decrease in QLQ for individual patient. For symptoms Mann Whitney Z test and for scores paired T test were applied.

Out of commonly observed adverse effects, 5 significant symptoms namely Stomatitis, Burning sensation, Dysphagia, Trismus, and Dryness of mouth were recorded in this study on the scale of grade 0-4. The mean of gradation was recorded before and after the treatment for all the patients.

Results:

Stomatitis—The symptom of stomatitis showed significant improvement (p=0.0041) from grade 2.3 to 1 after local application of the herbo-lipid composition of the present disclosure (FIG. 1).

Figure 2:
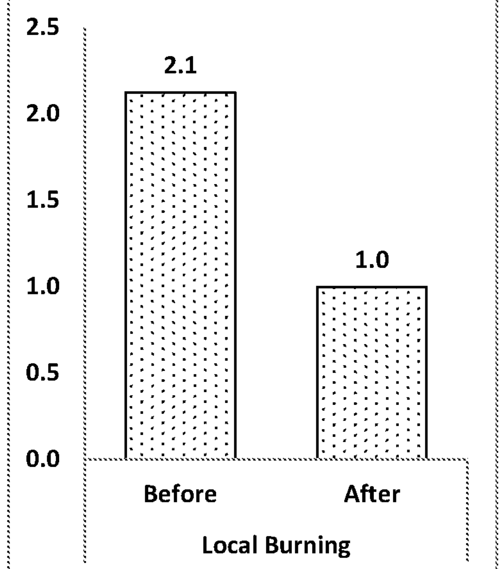
FIG. 2 depicts a graphical representation of the effect of the herbo-lipid composition on local burning in oral cancer patients undergoing radiotherapy.

Local Burning—The symptom of local burning in the oral cavity showed significant improvement (p=0.0019) from grade 2.1 to 1 after local application of the herbo-lipid composition of the present disclosure (FIG. 2).

Figure 3:
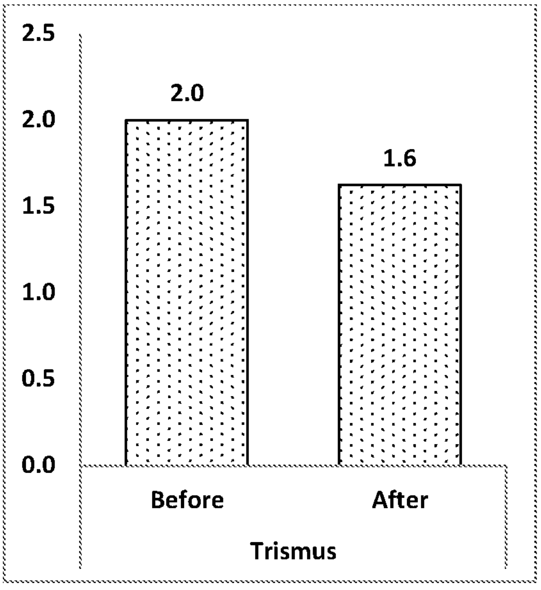
FIG. 3 depicts a graphical representation of the effect of the herbo-lipid composition on trismus in oral cancer patients undergoing radiotherapy.

Trismus—The symptom of trismus showed improvement from grade 2 to 1.6 after local application of the herbo-lipid composition of the present disclosure (FIG. 3).

Figure 4:
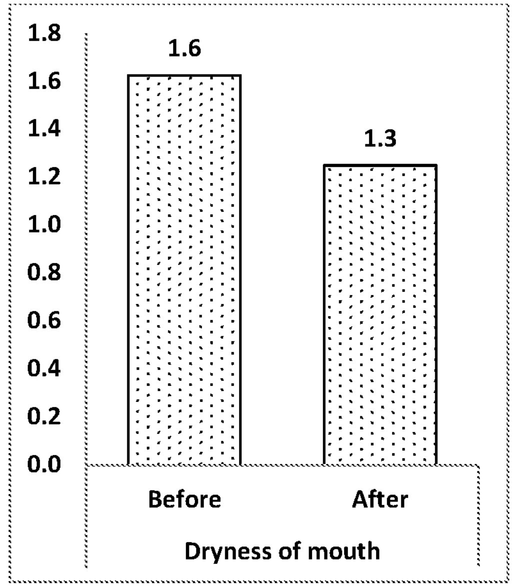
FIG. 4 depicts a graphical representation of the effect of the herbo-lipid composition on dryness of mouth in oral cancer patients undergoing radiotherapy.

Dryness of mouth—The symptom of dryness of mouth showed improvement from grade 1.6 to 1.3 after local application of the herbo-lipid composition of the present disclosure (FIG. 4).

Figure 5:
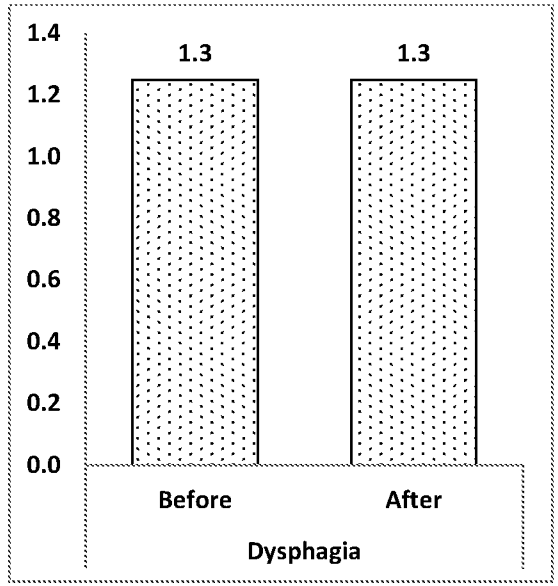
FIG. 5 depicts a graphical representation of the effect of the herbo-lipid composition on dysphagia in oral cancer patients undergoing radiotherapy.

Dysphagia—The symptom of dysphagia did not show any variation before and after local application of the herbo-lipid composition of the present disclosure (FIG. 5).

Figure 6:
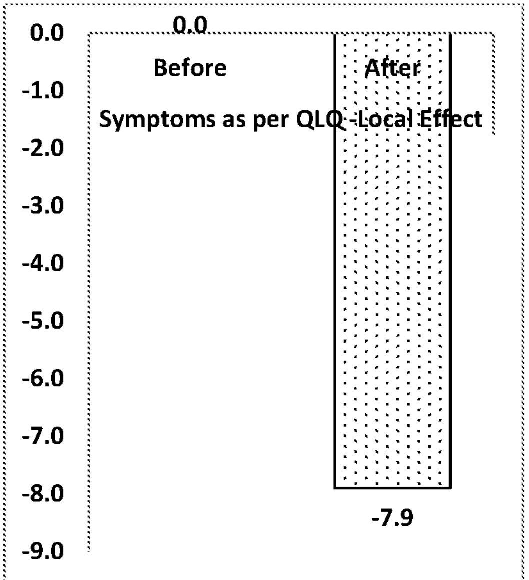
FIG. 6 depicts a graphical representation of the effect of the herbo-lipid composition on quality of life assessed using selected questions from QLQ H&N 24 for localized symptoms in oral cancer patients.

Assessment of local symptoms using selected QLQ questions: There was significant improvement (p=0.0017) in quality of life as assessed by patients themselves. Difference between the symptom scores before and after local application of the herbo-lipid composition of the present disclosure was observed to be (−7.9) indicating symptomatic relief (FIG. 6).

Experiment 2—Efficacy Studies of Local Application of the Herbo-Lipid Composition of the Present Disclosure on Radiotherapy Induced Local Adverse Effects in Cervix Cancer Patients The herbo-lipid composition of the present disclosure helps in alleviating local adverse effects of radiotherapy by local application in cervix cancer patients. To study this, the grades of adverse effects induced by radiotherapy were recorded before and after local application of the herbo-lipid composition of the present disclosure as per CTCAE version 4.03, as and when the effects appeared in the patients during and after radiotherapy.

In this study, 6 cervix cancer patients undergoing radiotherapy treatment were enrolled.

Assessment: Outcome Measures—

1. Assessment of adverse effects clinically and grading using CTCAE 4.03 Version (Grading of symptoms on 0 to 4 scales). Lower scale denotes less severity of the symptoms.
2. Assessment of Quality of Life (QoL) using selected questions (33-36, 41-43) applicable for assessment of local symptoms from Questionnaire—QLQ CX 24 of EORTC determined on the basis of patients' own perspective about her own well-being.

The assessment was performed before the start of the treatment and at the end of the treatment. The data was analyzed as mean values of grades of individual symptoms and increase/decrease in QLQ for individual patients. For symptoms Mann Whitney Z test and for scores paired 't' test were applied.

Out of commonly observed adverse effects, 7 significant symptoms, namely Per Vaginal Discharge, Foul smell through discharge, Itching, Local Burning, Burning micturition, burning at Anal Region and Bleeding piles were recorded in this study on the scale of grade 0-4. The mean of gradation before and after the treatment was recorded for all the patients.

Figure 7:
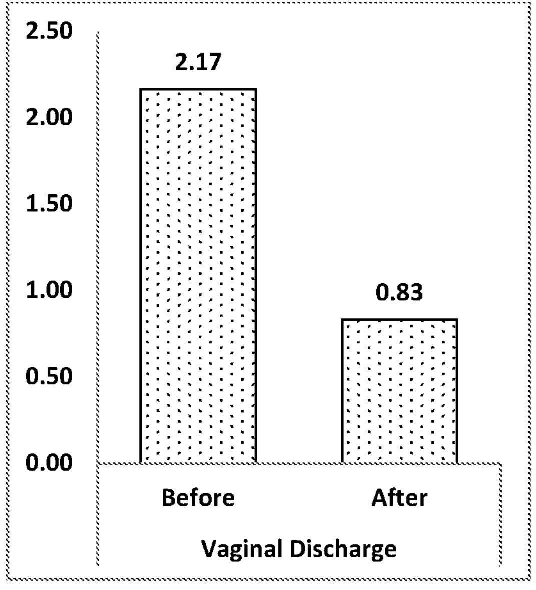
FIG. 7 depicts a graphical representation of the effect of the herbo-lipid composition on vaginal discharge in cervix cancer patients undergoing radiotherapy.

Results:

Vaginal Discharge—The symptom of vaginal discharge showed significant improvement (p=0.003) from grade 2.17 to 0.83 after local application of the herbo-lipid composition of the present disclosure (FIG. 7).

Figure 8:
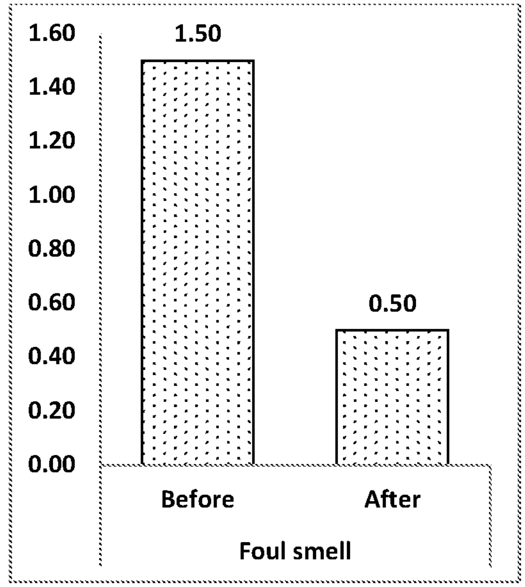
FIG. 8 depicts a graphical representation of the effect of the herbo-lipid composition on foul smell in cervix cancer patients undergoing radiotherapy.

Foul smell—The symptom of foul smell showed significant improvement (p=0.0098) from grade 1.5 to 0.5 after local application of the herbo-lipid composition of the present disclosure (FIG. 8)

Figure 9:
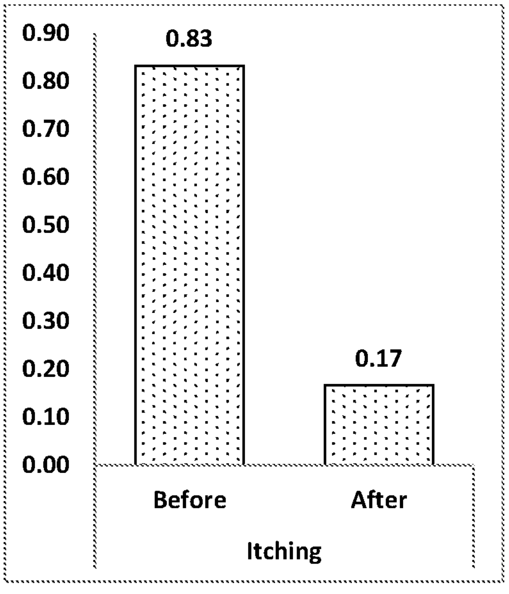
FIG. 9 depicts a graphical representation of the effect of the herbo-lipid composition on itching in cervix cancer patients undergoing radiotherapy.

Itching—The symptom of itching showed improvement from grade 0.8 to 0.1 after local application of the herbo-lipid composition of the present disclosure (FIG. 9)

Figure 10:
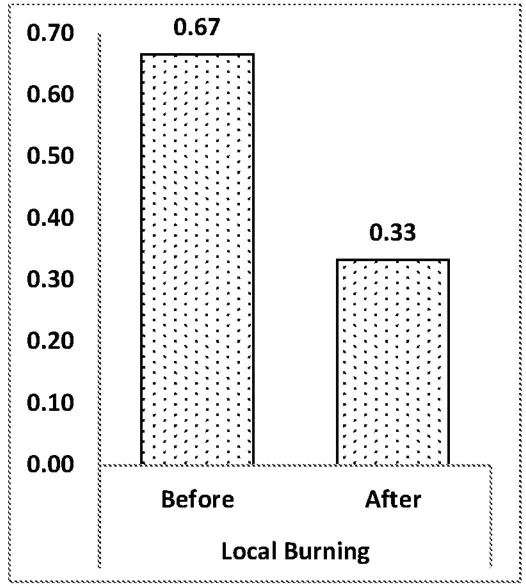
FIG. 10 depicts a graphical representation of the effect of the herbo-lipid composition on local burning in cervix cancer patients undergoing radiotherapy.

Local Burning—The symptom of local vaginal burning showed improvement from grade 0.6 to 0.3 after local application of the herbo-lipid composition of the present disclosure (FIG. 10)

Figure 11:
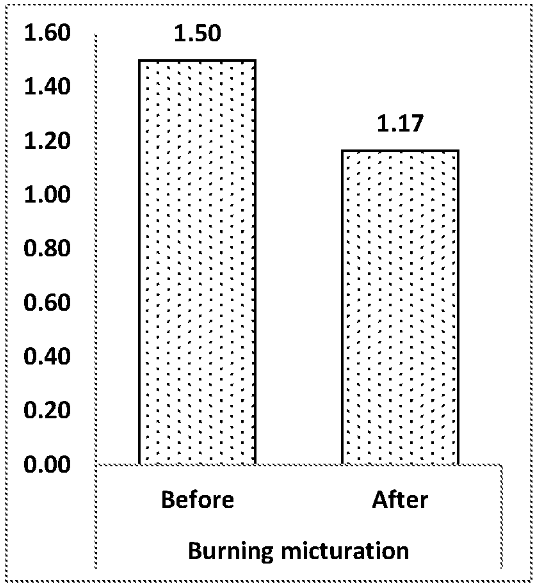
FIG. 11 depicts a graphical representation of the effect of the herbo-lipid composition on burning micturition in cervix cancer patients undergoing radiotherapy.

Burning Micturition—The symptom of burning micturition showed improvement from grade 1.5 to 1.17 after local application of the herbo-lipid composition of the present disclosure (FIG. 11)

Figure 12:
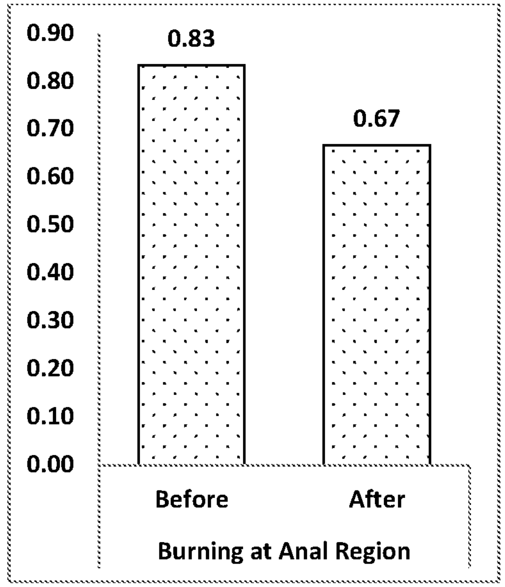
FIG. 12 depicts a graphical representation of the effect of the herbo-lipid composition on burning at anal region in cervix cancer patients undergoing radiotherapy.

Burning at Anal Region—The burning symptom at anal region showed improvement from grade 0.83 to 0.67 after local application of the herbo-lipid composition of the present disclosure (FIG. 12)

Figure 13:
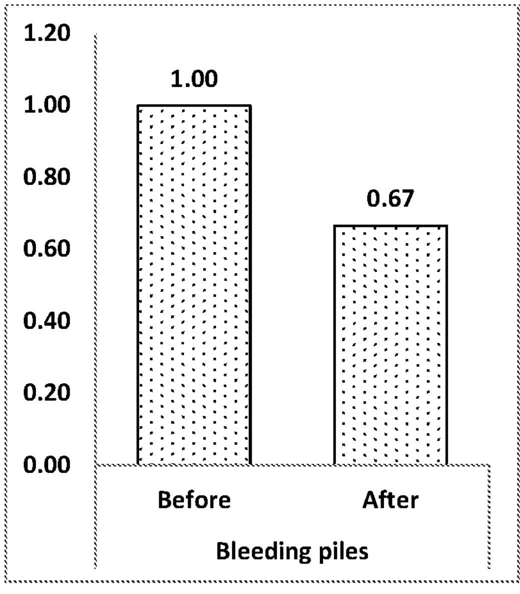
FIG. 13 depicts a graphical representation of the effect of the herbo-lipid composition on bleeding piles in cervix cancer patients undergoing radiotherapy.

Bleeding piles—The symptom bleeding piles showed improvement from grade 0.83 to 0.67 after local application of the herbo-lipid composition of the present disclosure (FIG. 13)

Figure 14:
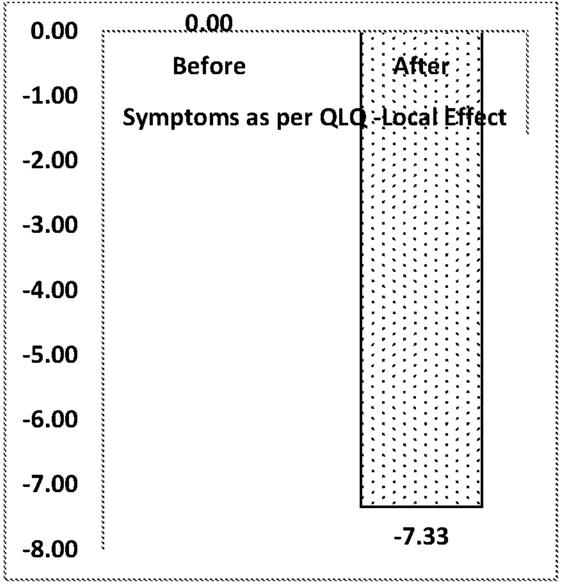
FIG. 14 depicts a graphical representation of the effect of the herbo-lipid composition on quality of life assessed using selected questions from QLQ CX 24 for localized symptoms in cervix cancer patients.

Assessment of local symptoms using selected QLQ questions: There was significant improvement (p=0.004) in the quality of life as assessed by patients themselves. The difference between the symptom scores before and after local application of the herbo-lipid composition of the present disclosure was observed to be (−7.33) indicating symptomatic relief (FIG. 14).

Overall, the herbo-lipid composition of the present disclosure shows better outcome imparting cooling effect in local adverse symptoms and quality of life in the patients suffering with oral and cervix cancer treated with radiotherapy.

Example 4: Efficacy Studies of the Herbo-Lipid Composition of the Present Disclosure in Various Types of Cancers The herbo-lipid composition of the present disclosure has the effect of reducing inflammation. As a consequence, it is beneficial in alleviating adverse effects of chemotherapy and radiotherapy as well as inflammatory conditions in various types of cancers when given with a specific set of other Ayurvedic medicines imparting synergistic effect. It also helps to improve quality of life of cancer patients.

Experiment 1—Efficacy Studies of Oral Administration of the Herbo-Lipid Composition of the Present Disclosure on Radiotherapy Induced Local Adverse Effects in Cervix Cancer Patients Radiotherapy is a treatment of choice in cervical cancer patients of all stages and grades. Radiotherapy causes various side-effects in cervical cancer patients, which is responsible for poor Quality of Life. It is observed that the oral administration of the herbo-lipid composition of the present disclosure helps in reducing side effects of radiotherapy. The herbo-lipid composition was given in 22 cervical cancer patients. To study the effect of this herbo-lipid composition, grade of adverse effects induced by radiotherapy was recorded before and after radiotherapy as per CTCAE version 4.03.

TABLE 2

Effect of the oral administration of herbo-lipid composition of the present disclosure in reducing disease related and radiation induced symptoms in cervical cancer patients
CA Cervix

| Symptoms | No. of patients in whom no symptoms developed during treatment (% Out of 22 patients) (A) | No. of patients with symptoms: No. of patients with reduction in symptoms after treatment (% Out of 22 patients) (B) | No change in symptoms after treatment | Aggravation in symptom after treatment | Significance for change in gradation of symptom | Total no. of patients benefited with PDK (% Out of 22 patients) (A + B) |
|---|---|---|---|---|---|---|
| Vaginal Discharge | 10 (45%) | 8 (36%) | 4 | 0 | 0.0007 | 18 (81%) |
| Burning sensation in vagina | 19 (86%) | 2 (9%) | 1 | 0 | 0.1 | 21 (85%) |
| Burning Micturition | 8 (36%) | 10 (45%) | 4 | 0 | 3.86E−05 | 18 (81%) |
| Dysuria | 17 (77%) | 5 (23%) | 0 | 0 | 0.0002 | 22 (100%) |
| Constipation | 9 (41%) | 8 (36%) | 5 | 0 | 0.003 | 17 (77%) |
| Painful and burning defecation | 10 (45%) | 7 (32%) | 5 | 0 | 0.002 | 17 (77%) |
| Diarrhoea | 14 (64%) | 7 (32%) | 1 | 0 | 2.9E−05 | 21 (96%) |
| P/R Bleeding | 18 (82%) | 4 (18%) | 0 | 0 | 0.002 | 22 (100%) |
| Pain in lower abdomen | 9 (41%) | 8 (36%) | 5 | 0 | 0.0008 | 17 (77%) |
| Pain in low back region | 12 (54%) | 5 (23%) | 5 | 0 | 0.035 | 17 (77%) |

Results—

In the present study, the oral use of the herbo-lipid composition of the present disclosure showed no development of symptoms at all, from 36% in case of burning micturition to 86% in burning sensation in vagina out of 22 cervical cancer patients before and after the treatment. Further, the treatment revealed reduction in already existing symptoms, ranging from 9% in case of burning sensation in vagina to 45% in case of burning micturition, out of the same 22 cervical cancer patients before and after the treatment.

Thus, 77% to 100% patients showed beneficial effects in various symptoms in response to the treatment. Out of the 10 symptoms studied, 5 symptoms such as vaginal discharge, burning micturition, dysuria, diarrhea and pain in lower abdomen depicted very highly significant reduction after the treatment. 3 symptoms, namely constipation, painful and burning defecation and par rectal bleeding and 1 symptom namely pain in low back showed highly significant and significant reduction, respectively, while only 1 symptom namely burning sensation in vagina did not show a significant reduction after the treatment. Overall, it can be stated that the treatment was mostly useful for not producing any disease related or radiation induced symptoms in cervical cancer patients, while for those who had symptoms before treatment showed significant reduction in these symptoms.

Experiment 2—Efficacy Studies of Oral Administration of the Herbo-Lipid Composition of the Present Disclosure on Chemotherapy Induced Adverse Effects in Ovarian Cancer Patients Ovarian cancer patients are commonly treated with surgery followed by chemotherapy, which causes various adverse effects. It is observed that the herbo-lipid composition of the present disclosure helps in reducing side effects of chemotherapy when given in 16 ovarian cancer patients. To study the effect of this herbo-lipid composition, grade of adverse effects induced by chemotherapy was recorded before and after chemotherapy as per CTCAE version 4.03.

TABLE 3

Effect of the oral administration of herbo-lipid composition of the present disclosure in reducing disease related and chemotherapy induced symptoms in ovarian cancer patients CA Ovary

| | No. of patients | No. of patients with symptoms | | | | |
|---|---|---|---|---|---|---|
| Symptoms | in whom no symptoms developed during treatment (% Out of 16 patients) (A) | No. of patients with reduction in symptoms after treatment (% Out of 16 patients) (B) | No change in symptoms after treatment | Aggravation in symptom after treatment | Significance for change in gradation of symptom | Total no. of patients benefited with PDK (% Out of 16 patients) (A + B) |
| Burning micturition | 9 (56%) | 7 (44%) | 0 | 0 | 0.00566714 | 16 (100%) |
| Burning in anal region | 13 (81%) | 2 (12%) | 1 | 0 | 0.230199641 | 15 (93%) |
| Loss of appetite | 7 (44%) | 5 (31%) | 3 | 1 | 0.085115503 | 12 (75%) |
| Constipation | 11 (69%) | 3 (18%) | 2 | 0 | 0.066688 | 14 (87%) |
| Burning in lower extremities | 14 (87%) | 2 (12%) | 0 | 0 | 0.292893219 | 16 (100%) |
| Burning in whole body | 13 (81%) | 2 (12%) | 1 | 0 | 0.158302423 | 15 (93%) |
| Stomatitis | 14 (87%) | 1 (6%) | 1 | 0 | 0.422649731 | 15 (93%) |

Results—

In the present study, the oral use of the herbo-lipid composition of the present disclosure showed no development of chemotherapy induced adverse symptoms ranging from 44% in case of loss of appetite to 87% in case of stomatitis out of 16 ovarian cancer patients before and after the treatment. Further, the treatment revealed reduction in already existing symptoms, ranging from 6% in case of stomatitis to 44% in case of burning micturition, out of 16 ovarian cancer patients before and after the treatment. Thus, 75% to 100% patients showed beneficial effects in various symptoms in response to the treatment. Out of the 7 symptoms studied, 3 symptoms such as burning micturition, loss of appetite and constipation depicted very highly significant reduction after the treatment. Remaining symptoms were also show remarkable reduction, but not statistically significant. Overall, it can be stated that the treatment was mostly useful for not producing any disease related or chemotherapy induced symptoms in ovarian cancer patients, while for those who had symptoms before treatment showed significant reduction in these symptoms.

Experiment 3—Efficacy Studies of Oral Administration of the Herbo-Lipid Composition of the Present Disclosure on Chemotherapy Induced Adverse Effects in Colorectal Cancer Patients Colorectal cancers are usually treated with surgery and/or chemotherapy (parental/oral). Chemotherapy induces various side-effects hampering quality of life of patients. It is observed that the herbo-lipid composition of the present disclosure helps in reducing side effects of chemotherapy when given in 12 colorectal cancer patients. To study this effect, grades of adverse effects induced by chemotherapy were recorded before and after chemotherapy as per CTCAE version 4.03.

TABLE 4

Effect of the oral administration of herbo-lipid composition of the present disclosure in reducing disease related and chemotherapy induced symptoms in colorectal cancer patients Colorectal cancers

| Symptoms | No. of patients in whom no symptoms developed during treatment (% Out of 12 patients) (A) | No. of patients with symptoms: No. of patients with reduction in symptoms after treatment (% Out of 12 patients) (B) | No change in symptoms after treatment | Aggravation in symptom after treatment | Significance for change in gradation of symptom | Total no. of patients benefited with PDK (% Out of 12 patients) (A + B) |
|---|---|---|---|---|---|---|
| Stool with mucous | 9 (75%) | 2 (17%) | 0 | 1 | 1 | 11 (92%) |
| Loose motion | 6 (42%) | 3 (25%) | 2 | 2 | 0.72 | 9 (75%) |
| Burning sensation at anal region | 10 (83%) | 0 (0%) | 2 | 0 | — | 10 (83%) |
| Par rectal bleeding | 9 (75%) | 3 (25%) | 0 | 0 | — | 12 (100%) |
| Constipation | 9 (75%) | 2 (17%) | 1 | 0 | 0.12 | 11 (92%) |
| Stomatitis | 9 (75%) | 2 (17%) | 1 | 0 | 0.23 | 11 (92%) |
| Weakness | 0 (0%) | 8 (68%) | 4 | 0 | 0.01 | 8 (67%) |
| Loss of appetite | 3 (25%) | 6 (51%) | 3 | 0 | 0.01 | 9 (75%) |

Results—

In the present study, use of the herbo-lipid composition of the present disclosure showed no development of chemotherapy induced adverse symptoms ranging from 0% in case of weakness 83% in case of burning sensation in anal region (out of 12 colorectal cancer patients before and after the treatment. Further, the treatment revealed reduction in already existing symptoms, ranging from 0% in case of burning sensation in anal region to 68% in case of weakness, out of 12 colorectal cancer patients before and after the treatment. Thus, 67% to 100% patients showed beneficial effects in various symptoms in response to the treatment. Out of the 8 symptoms studied, 2 symptoms such as weakness and loss of appetite depicted very highly significant reduction after the treatment. Remaining symptoms also showed remarkable reduction, but not statistically significant. Overall, the treatment was mostly useful for not producing any disease related or chemotherapy induced symptoms in colorectal cancer patients, while for those who had symptoms before treatment showed significant reduction in these symptoms.

Experiment 4—Efficacy Studies of Oral Administration of the Herbo-Lipid Composition of the Present Disclosure Given for Longer Duration in Maintaining Wellbeing and Quality of Life in Various Types of Cancer Patients Clinically, it was observed that the present herbo-lipid composition when given for a long duration helped in maintaining wellbeing and quality of life of patient in various types of cancer patients. To study these effects, assessment of performance status was done using Karnofsky score (Grading for well-being on 0 to 100 scale, the higher score denotes better performance), assessment of Quality of Life (QoL) using Questionnaire QLQ C30 (designed for all types of cancers) and assessment of disease related status using specific disease related questionnaire of EORTC. These QLQ give a perspective of wellbeing on the basis of patients' own viewpoint. QLQ C30 gives perspective of symptomatology (Symptom score), ability to perform routine activities (Functional score) and overall well-being (Global score). Weight being an important parameter to assess wellbeing of cancer patients, it was also analyzed in these patients. These parameters were recorded before and after consumption of the present herbo-lipid composition.

TABLE 5

Effect of oral administration of herbo-lipid composition of the present disclosure in maintaining wellbeing and quality of life in various types of cancer patients
All types of Cancers

| Type of Cancer | Sr. No. | Diagnosis with HPR | Stage/ Grade | Duration ofPDG composition and period of observation in weeks | Weight | | Karnofsky | | QLQ (Functional score) |
|---|---|---|---|---|---|---|---|---|---|
| | | | | | Before | After | Before | After | Before |
| CA Cervix | 1 | Poorly differentiated KERATINIZING SCC | IV/III | 71 | 77.3 | 75.8 | 70 | 90 | 62.22 |
| | 2 | Poorly differentiated KERATINIZING SCC | IIIB/III | 59 | 64 | 64 | 70 | 80 | 66.67 |
| | 3 | with Ca Ovary SCC - cervix + granulosa cell tumour ovary | IV/NA | 46 | 50 | 53 | 70 | 70 | 77.78 |
| Oral cavity cancer | 1 | Ca Rt Cheek - Moderately differentiated SCC | III/III | 95 | 73.3 | 71.5 | 80 | 80 | 80.00 |
| | 2 | Ca Soft Palate - SCC | III/II | 81 | 53 | 53 | 70 | 80 | 40.00 |
| | 3 | Ca Buccal Mucosa (Rt.) | IVA/NA | 56 | 52 | 72 | 60 | 80 | 33.33 |
| | 4 | CA Base of the tongue - Poorly differentated SCC | III/III | 52 | 60 | 59 | 70 | 80 | 53.33 |
| Ca Breast | 1 | Intraductal carcinoma 1/5 LN mets | II/NA | 84 | 98 | 100 | 80 | 90 | 95.56 |
| | 2 | Infiltrating duct cell carcinoma | II/II | 78 | 44.5 | 50.5 | 70 | 80 | 51.11 |
| | 3 | Infiltrating duct cell carcinoma | II/III | 67 | 58 | 54 | 70 | 90 | 37.78 |
| | 4 | Infiltrating duct carcinoma | IIB/II | 45 | 61 | 58 | 80 | 90 | 55.56 |
| CA Oesophagus | 1 | Infiltrating squamous cell carcinoma | IB/II | 40 | 63 | 66 | 80 | 90 | 60.00 |
| CA Rectum | 1 | Invasive adenocarcinoma (Moderately Differentiated) | IIA/III | 46 | 65 | 65 | 70 | 70 | 60.00 |
| CA Brain | 1 | Glioblastoma multiforme (Rt temporal region) | NA/IV | 26 | 64 | 64 | 80 | 90 | 40.00 |
| NHL | 1 | Abdominal Lump with bone marrow involvement | IV/ Aggressive | 54 | 65 | 71.5 | 80 | 90 | 66.67 |
| | 2 | Malignant lymphoma- Rt supraclavicular. No involvemet of bone marrow | III/ Aggressive | 40 | 73 | 73 | 80 | 90 | 66.67 |
| | | Statistical significance | | | NS | | *** | | *** |

TABLE 5-continued

Effect of oral administration of herbo-lipid composition of the present disclosure in maintaining wellbeing and quality of life in various types of cancer patients
All types of Cancers

| Type of Cancer | Sr. No. | QLQ (Functional score) After | QLQ (Symptom score) Before | QLQ (Symptom score) After | QLQ (Global score) Before | QLQ (Global score) After | QLQ (Specific for affected organ) Before | QLQ (Specific for affected organ) After |
|---|---|---|---|---|---|---|---|---|
| CA | 1 | 97.78 | 28.21 | 5.13 | 66.67 | 100.00 | 45 | 30 |
| Cervix | 2 | 95.56 | 23.08 | 10.26 | 66.67 | 100.00 | 40 | 26 |
| | 3 | 95.56 | 12.82 | 10.26 | 66.67 | 100.00 | 35 | 24 |
| Oral | 1 | 88.89 | 28.21 | 2.56 | 50.00 | 50.00 | 70 | 64 |
| cavity | 2 | 66.67 | 43.59 | 25.64 | 50.00 | 66.67 | 57 | 50 |
| cancer | 3 | 66.67 | 51.28 | 17.95 | 66.67 | 83.33 | 60 | 52 |
| | 4 | 66.67 | 38.46 | 20.51 | 66.67 | 83.33 | 80 | 50 |
| Ca | 1 | 97.78 | 10.26 | 2.56 | 50.00 | 83.33 | 20 | 18 |
| Breast | 2 | 86.67 | 25.64 | 2.56 | 83.33 | 83.33 | 30 | 17 |
| | 3 | 53.33 | 46.15 | 46.15 | 33.33 | 41.67 | 22 | 20 |
| | 4 | 71.11 | 30.77 | 28.21 | 33.33 | 41.67 | 32 | 25 |
| CA Oesophagus | 1 | 80.00 | 23.08 | 12.82 | 66.67 | 83.33 | 32 | 25 |
| CA Rectum | 1 | 77.78 | 30.77 | 12.82 | 66.67 | 83.33 | 38 | 32 |
| CA Brain | 1 | 55.56 | 30.77 | 17.95 | 50.00 | 66.67 | 28 | 25 |
| NHL | 1 | 71.11 | 17.95 | 10.26 | 50.00 | 66.67 | 0 | 0 |
| | 2 | 77.78 | 23.08 | 12.82 | 66.67 | 83.33 | 0 | 0 |
| Statistical significance | | *** | *** | | *** | | *** | |

Results—

Extremely significant results were obtained in Karnofsky score, symptom score, function score, global score and disease specific score of QLQ with the use of the present herbo-lipid composition.

These results indicate that the herbo-lipid composition of the present disclosure when given for long duration (more than 40 weeks) gives a better outcome in maintaining wellbeing and quality of life in the patients suffering from various types of cancers even in the advance stage The same studies were carried out for the herbo-lipid composition of the batch of the finished product 2 and 3. The results for the batch of finished product 2 and 3 are found to be similar like batch 1 composition.

TECHNICAL ADVANCEMENTS

The present disclosure described herein above has several technical advantages including, but not limited to, the realization of a herbo-lipid composition:

- that produces enhanced anti-inflammatory response;
- that alleviates the disease induced symptoms and also radiotherapy/chemotherapy induced side effects in cancer using both, orally and/or locally; and
- that improves quality of life of cancer patients undergoing radiotherapy/chemotherapy when given orally and/or locally.

The embodiments as described herein above, and various features and advantageous details thereof are explained with reference to the non-limiting embodiments in the description. Descriptions of well-known aspects, components and molecular biology techniques are omitted so as to not unnecessarily obscure the embodiments herein.

The foregoing description of specific embodiments so fully reveals the general nature of the embodiments herein, that others can, by applying current knowledge, readily modify and/or adapt for various applications of such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein. Further, it is to be distinctly understood that the foregoing descriptive matter is to be interpreted merely as illustrative of the disclosure and not as a limitation.

Having described and illustrated the principles of the present disclosure with reference to the described embodiments, it will be recognized that the described embodiments can be modified in arrangement and detail without departing from the scope of such principles.

While considerable emphasis has been placed herein on the particular features of this disclosure, it will be appreciated that various modifications can be made, and that many changes can be made in the preferred embodiment without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

The invention claimed is:

1. A herbo-lipid composition for alleviating radiotherapy or chemotherapy induced adverse effects in cancer patients, said herbo-lipid composition comprising:

a) an extract of petals and stalks of Padmak;
b) an extract of whole Durva plant;
c) a decoction of roots of Ananta; and d) Ghee obtained from cow's milk in an amount ranging from 90 wt % to 98 wt % of the total weight of the composition;

wherein the weight ratio of said extract of petals and stalks of Padmak to said extract of whole Durva plant to said decoction of roots of Ananta is 1:1:1;

wherein said extract of Padmak, said extract of Durva, and said decoction of Ananta are independently obtained by using at least one solvent selected from the group consisting of alcohol, water, and a mixture thereof; and said composition is in the form of a thick viscous liquid.

2. The composition as claimed in claim 1, wherein the amount of the combined extracts of petals and stalks of Padmak, whole Durva plant, and roots of Ananta is in the range of 2 wt % to 10 wt % of the total weight of the composition.

3. The composition as claimed in claim 1, wherein said composition is used for alleviating symptoms in erythematous skin rash, alleviating radiotherapy or chemotherapy induced adverse effects in an oral cancer patient, in a cervical cancer patient, in an ovarian cancer patient, and a colorectal cancer patient.

4. A process for preparing a herbo-lipid composition as claimed in claim 1, wherein said process comprises the following steps:

i. blending an extract of petals and stalks of Padmak, an extract of whole Durva plant, and decoction of roots of Ananta in a predetermined amount of Ghee to obtain a mixture; and ii. heating said mixture for a predetermined time to remove solvents present in said extracts to obtain the herbo-lipid composition in the form of thick viscous liquid, wherein the weight ratio of said extract of Padmak to said extract of Durva to said decoction of Ananta is 1:1:1, and wherein the predetermined amount of Ghee is in the range of 90% to 98% of the total weight of the composition.

5. The process as claimed in claim 4, wherein said heating is carried out at a temperature in the range of 60° C. to 120° C. and said predetermined time is in the range of 30 minutes to 90 minutes.

6. The process as claimed in claim 4, wherein said process includes a pre-step of obtaining said extract of petals and stalk of Padmak comprising:

a) obtaining petals and stalk of flowers of Padmak;

b) blending the chopped petals and stalks of flowers of Padmak in an aqueous or hydroalcoholic solvent to obtain grinded petals and stalks of flowers of Padmak; and c) filtering said blend to obtain a filtrate containing the extract of petals and stalk of Padmak, wherein the ratio of the petals of Padmak to the stalk of Padmak is 3:1, and wherein the ratio of the petals and stalks of Padmak to the solvent is 1:1.25.

7. The process as claimed in claim 4, wherein said process includes a pre-step of obtaining said extract of whole Durva plant comprising:

a. obtaining whole Durva plant;

b. chopping and blending whole Durva plant in an aqueous or hydroalcoholic solvent to obtain a blended Durva plant; and c. filtering said blend to obtain a filtrate containing the extract of whole Durva plant, wherein the ratio of the whole plant of Durva to the solvent is 1:2.

8. The process as claimed in claim 4, wherein said process includes a pre-step of obtaining said decoction of roots of Ananta:

A. obtaining roots of Ananta;

B. pulverizing roots of Ananta to obtain coarse powder and soaking in aqueous/or hydroalcoholic solvent to obtain a mixture;

C. decocting said roots of Ananta in an aqueous or hydroalcoholic solvent to obtain a decoction; and D. filtering said decoction to obtain a filtrate containing the decoction of Ananta, wherein the ratio of Ananta to an aqueous or hydroalcoholic solvent is 1:8, and wherein said decoction is carried out at a temperature in the range of 80° C. to 120° C.

* * * * *